United States Patent
Niazi

(10) Patent No.: US 8,685,245 B2
(45) Date of Patent: Apr. 1, 2014

(54) CONCENTRATOR FILTER

(75) Inventor: Sarfaraz Niazi, Deerfield, IL (US)

(73) Assignee: Therapeutic Proteins International, LLC, Chicago, IL (US)

(*) Notice: Subject to any disclaimer, the term of this patent is extended or adjusted under 35 U.S.C. 154(b) by 0 days.

(21) Appl. No.: 13/149,856

(22) Filed: May 31, 2011

(65) Prior Publication Data

US 2011/0290745 A1     Dec. 1, 2011

Related U.S. Application Data

(62) Division of application No. 13/093,859, filed on Apr. 26, 2011.

(51) Int. Cl.
*B01D 29/54* (2006.01)
*B01D 29/62* (2006.01)
*B01D 35/00* (2006.01)

(52) U.S. Cl.
USPC ........ 210/323.1; 210/151; 210/200; 210/209; 210/221.2; 210/252; 210/258; 210/314; 210/323.2; 210/333.01; 210/411; 210/416.1; 210/486; 210/500.1; 210/500.27

(58) Field of Classification Search
USPC .......... 210/200–203, 209, 220, 221.1–221.2, 210/252–257.2, 258, 275, 314, 319, 323.1, 210/323.2, 333.01, 340, 344, 391, 393, 407, 210/408, 411, 416.1, 486, 488, 496, 500.1, 210/500.27, 503, 504, 506, 321.6, 321.79, 210/321.8, 321.88, 321.89, 500.23, 151
See application file for complete search history.

(56) References Cited

U.S. PATENT DOCUMENTS

| | | | | |
|---|---|---|---|---|
| 3,968,034 A * | 7/1976 | Tymoszczuk | ............... | 210/618 |
| 5,236,595 A * | 8/1993 | Wang et al. | ............... | 210/669 |
| 6,193,890 B1 * | 2/2001 | Pedersen et al. | ............ | 210/636 |
| 6,245,239 B1 * | 6/2001 | Cote et al. | ............... | 210/636 |
| 6,303,035 B1 * | 10/2001 | Cote et al. | ............... | 210/636 |
| 6,375,848 B1 * | 4/2002 | Cote et al. | ............... | 210/650 |
| 6,613,222 B2 * | 9/2003 | Mikkelson et al. | ......... | 210/138 |
| 7,179,370 B2 * | 2/2007 | Dimitriou et al. | ........... | 210/151 |
| 7,241,382 B2 * | 7/2007 | Gordon | ............... | 210/209 |
| 7,468,082 B2 * | 12/2008 | Gordon | ............... | 55/302 |
| 7,981,301 B2 * | 7/2011 | Powell | ............... | 210/748.01 |
| 8,246,827 B2 * | 8/2012 | Chen et al. | ............... | 210/321.8 |
| 2006/0000775 A1 | 1/2006 | Zha et al. | | |
| 2008/0302713 A1 | 12/2008 | Patrick | | |
| 2010/0108621 A1 | 5/2010 | Zainiev | | |
| 2011/0117538 A1 | 5/2011 | Niazi | | |
| 2011/0201050 A1 | 8/2011 | Niazi | | |

OTHER PUBLICATIONS

International Search Report and Written Opinion for PCT/US12/39109, dated Aug. 17, 2012.

* cited by examiner

*Primary Examiner* — John Kim
(74) *Attorney, Agent, or Firm* — Therapeutic Proteins International, LLC; Cheryl Liljestrand; Sarfaraz K. Niazi

(57) ABSTRACT

A method and an apparatus for separating suspended matter from liquid includes a concentrator filter that draws the liquid out of the suspension while the filter kept unblocked by a sparging filter that allows scrubbing of the concentrator filter by gas bubbles. This invention can be used to replace cross-flow filtration and centrifugation in the bioprocess industry and to reduce the volume of suspensions to concentrate the yield of the end product in the chemical industry.

6 Claims, 3 Drawing Sheets

CONCENTRATOR FILTER

TECHNICAL FIELD OF THE INVENTION

The present invention relates to the field of filtering, more precisely to a method and an apparatus for the separation of suspended matter from liquid and the use of said method and apparatus.

BACKGROUND OF THE INVENTION

Separation of suspended matter from liquid is known in the art. Methods such as precipitation, centrifugation and filtering are commonly used for separation purposes in a vast number of industries including chemical and bioprocess industry. The latter separation method is relevant for the present invention.

Several problems concerning the separation of suspended matter from liquid exist, most significantly the blocking of the filter material used that requires replacement of filters, prolong filtration cycles, use of additional containers and eventually high cost. In those instances where the suspended material is a biological entity, the current methods include either centrifugation of the suspended entities or the use of cross-flow filtration methods to reduce the volume, both of which are cumbersome, require large vessels for receiving the filtrate and frequently strain the material contained in the solution causing significant decrease in the productivity of the process.

Centrifugation is a very expensive separation method. When filtering liquids having a high suspended matter content there are significant problems concerning accumulation of suspended matter on the filter. This accumulation is known as the filter cake. In conventional methods the filter cake will grow until further filtering is impossible and the filter then has to be cleaned. There are various techniques for limiting the filter cake. One such technique is cross-flow. Here, the filter is kept clean by continuously scrubbing it with high-speed gas bubbles.

Another filtering method is back flushing. Here, the movement of the suspension is reversed to lift the filter cake from the filter. When using the cross-flow or back flushing methods the filter cake is not accumulated on the filter but is accumulated in the suspension. This requires the filtering process to be either stopped or for the existence of an outlet for the accumulated suspended matter. In the latter situation the removed suspended matter will still have a relatively high liquid content.

A further filtering method is flushing. The filtering process is stopped and the filter is washed. Here, the suspended matter is accompanied by a lot of liquid.

The above problems are overcome by the present invention by presenting a method and an apparatus capable of continuously removing suspended matter from a liquid, and thereby provide a method and apparatus capable of operating continuously without getting and at the same time having an increased filtering capacity and a economical advantage over the prior art.

SUMMARY OF THE INVENTION

The present invention concerns a method for separating suspended matter from liquid, comprising the steps of i) providing a concentrator filter comprising a solid material with a hollow inner volume; ii) providing a means of scrubbing the concentrator filter by sparging the concentrator filter with high-speed gas bubble that can remove any particles that adhere to the concentrator filter; iii) contacting the concentrator filter with sparging filter such that there is maximum contact of surface or at least very close proximity of the two filter; iv) sparging the concentrator filter as the liquid enters the concentrator filter by vacuum; v) continuing the process until the desire volume of liquid is removed from the suspension.

BRIEF DESCRIPTION OF THE DRAWINGS

FIG. 1 (b) is the top view of the tip of the filter assembly showing the arrangement of the concentrator filter and the sparging filter.

FIG. 3 (b) is the top view of the tip of the filter assembly showing the arrangement of the concentrator filter and three sparging filters.

DETAILS OF THE INVENTION

Figure 1B:
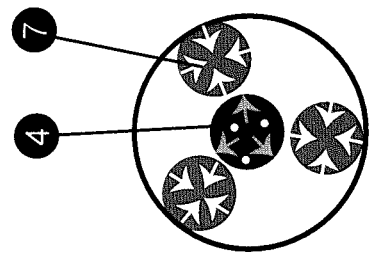
FIG. 1 (a) is the side view of a filter assembly containing concentrator filter and sparging filter surrounding the concentrator filter.

Filtration is the process of separating suspended solid matter from a liquid, by causing the latter to pass through the pores of some substance, called a filter. The liquid that has passed through the filter is called the filtrate. The filter may be paper, cloth, cotton-wool, asbestos, slag- or glass-wool, unglazed earthenware, sand, or other porous material.

Filtration is very frequently employed in chemical technology, and it often presents great difficulties. In most technical operations, cotton cloth is the filtering material, but occasionally woolen or haircloth is necessary. The cloth may be fastened on a wooden frame in such a way that a shallow bag is formed, into which the turbid liquid is poured. The filtrate, in this ease, is cloudy at first, but soon becomes clear, and then the turbid portion is returned to the filter. Filtration is often retarded by the presence of fine, slimy precipitates, or by the formation of crystals in the interstices of the cloth, from the hot solution. Any attempt to hasten filtration, by scraping or stirring the precipitate on the cloth, will always cause the filtrate to run turbid.

A better form is the "bag-filter," which is a long, narrow hag of twilled cotton, supported by an outside cover of coarse, strong netting, capable of sustaining a considerable weight and hydrostatic pressure. These bags are often five or six feet long, and eight inches or more in diameter. The open end of the bag is tied tightly around a metallic ring or a nipple, by which the whole is suspended, and through which the liquor to be filtered is introduced. When hot liquids are filtered, the bags are often hung in steam-heated rooms, the temperature being nearly that of the liquid.

In pressure filtration, the liquid is forced through the interstices of the filter by direct atmospheric pressure, the air being exhausted from the receiver; or by hydrostatic pressure, obtained either by means of a high column of the liquid, or by a force pump. By the first method, called suction filtration, the liquid may be forced downward through the filter into a receiver; the precipitate collects on the top of the filter and becomes a part of the filtering layer. This sometimes causes difficulty, for the particles of certain precipitates unite to form an impervious layer. Or the filtrate may be drawn upwards through the filter, which is suspended in the liquid to be filtered; thus clogging does not occur so easily, as a large part of the precipitate settles to the bottom of the vessel and does not come in contact with the filter until most of the liquid has been drawn off.

In technical work, the filter press usually obtains pressure. This is a strong iron frame, in which a number of cast-iron or bronze filter cells are supported. Each cell is made up of two flat metal plates with raised edges, separated by a hollow "distance frame" of the same metal. There is a hole in the centre of each plate, and grooves on each surface leading to an opening at the lower edge of the plate. A filter is made of two pieces of cloth, slightly larger than the plates, sewed together along the margin of a small circular opening cut in the centre of each. One piece of the cloth is passed through the hole in the plate, and then both pieces are spread out smoothly, one on either side of the plate.

Another plate is prepared in the same way, and a distance frame having been placed between them, the cell thus formed is set vertically in the press frame, where it is supported by lugs on each plate and distance frame. When the desired number of cells are ready, they are tightly clamped together by means of a heavy screw, which passes through one end of the press frame. Thus a series of cells, lined with filter cloth and connected by a straight channel through the central holes, is formed. A powerful force pump drives the liquid to be filtered into the cells, where it passes from one to the other until they are all filled. The hydrostatic pressure forces the liquid through the filters into the grooves in the plates, along which it flows, and escapes through the openings at the lower side of the plate. The sediment retained by the cloth collects ill the cell and forms a solid cake, which finally fills each cell completely. The process is then stopped, the cells taken apart, and the cake of sediment having been removed, the cells are returned to the press frame, to be again put into operation. The filtrate is caught in a trough.

In another form of press, instead of the central opening, there is a hole in the cornel of each plate and distance frame in such a position that, when placed in the press, the holes form a continuous channel through the corner of the whole series of cells. A small hole drilled on the inside of each distance frame, at right angles to the direction of the channel, admits the liquid into each cell. The filter is a piece of cloth hung over the distance frame in such a way that both sides of the frame are covered. A frame so covered is put between each pair of grooved plates. Small holes are cut in the cloth to correspond to the channel in the corners of the cells. The method of filtration is the same as in the central feed machines.

The pressure obtained by the force pump may be only a few pounds, or it may rise to several hundred pounds per square inch. The filter press may contain from a dozen to fifty or more cells, and these cells may be as large as four feet in diameter. For many purposes the press is surrounded by coils or jackets, through which steam or refrigerating solutions may be circulated, according as hot or cold filtration is desired. The filter press is very rapid in its action and is extensively employed in industrial chemical work. For use with acid or corrosive liquids, the plates and distance frames are often covered with lead or some alloy, which is not easily corroded.

The centrifugal machine is, to a great extent, replacing the filter press and other filters, especially when crystals are to be removed. This furnishes the most rapid method and leaves the substance almost dry. The centrifugal machine is a cylindrical box or basket of wire gauze or perforated sheet metal, fixed to a vertical shaft, which rotates at a very high speed. The contents of the box are driven to the outer wall by the centrifugal force, the solid matter being retained by the gauze or screen. The liquid passes through and is caught in a fixed shell, surrounding the rotating basket. These machines are of various sizes from 12 to 60 inches diameter, and 8 to 36 inches, depth of basket. Two general forms are in use: the over-driven type, in which the driving pulley is fixed at the upper end of the shaft, above the basket; and the under-driven type, in which the basket is placed on the upper end of the shaft, and the pulley below. In the over-driven type it is frequently customary to suspend the shaft in flexible bearings. Thus the basket is enabled to adjust itself to any change in the centre of gravity, caused by unequal loading, and runs without vibration.

Sand filters are sometimes used for work on a large scale. These are made as follows: into a box having a perforated bottom, is put a layer of coarse gravel; this is covered with finer pebbles; these by sand, and a jute or canvas cloth covers the whole. A wooden or iron grating is added to protect the filter, when the sediment is shoveled out. The filter is often placed over a receptacle from which the air may be exhausted, thus affording pressure filtration if necessary.

Bioprocessing requires intensive use of filtration, from sterilizing liquids to separating cells and organisms and to reduce the volume of liquid prior to subjecting it to purification steps.

One of the most common techniques used in the art of bioreaction is to separate the bacteria or cells after the bioreaction cycle completes. In most instances, this would require using very high-speed centrifuges to separate the very fine cells. A centrifuge uses centrifugal force (g-force) to isolate suspended particles from their surrounding medium on either a batch or a continuous-flow basis. Applications for centrifugation are many and may include sedimentation of cells and viruses, separation of subcellular organelles, and isolation of macromolecules such as DNA, RNA, proteins, or lipids.

Many particles or cells in a liquid suspension, given time, will eventually settle at the bottom of a container due to gravity (1×g). However, the length of time required for such separations is impractical. Other particles, extremely small in size, will not separate at all in solution, unless subjected to high centrifugal force. When a suspension is rotated at a certain speed or revolutions per minute (RPM), centrifugal force causes the particles to move radially away from the axis of rotation. The force on the particles (compared to gravity) is called Relative Centrifugal Force (RCF). For example, an RCF of 500×g indicates that the centrifugal force applied is 500 times greater than earth's gravitational force.

In differential centrifugation separation is achieved primarily based on the size of the particles in differential centrifugation. This type of separation is commonly used in simple pelleting and in obtaining partially-pure preparation of subcellular organelles and macromolecules. For the study of subcellular organelles, tissue or cells are first disrupted to release their internal contents. This crude disrupted cell mixture is referred to as a homogenate. During centrifugation of a cell homogenate, larger particles sediment faster than smaller ones and this provides the basis for obtaining crude organelle fractions by differential centrifugation. A cell homogenate can be centrifuged at a series of progressively higher g-forces and times to generate pellets of partially-purified organelles.

When a cell homogenate is centrifuged at 1000×g for 10 minutes, unbroken cells and heavy nuclei pellet to the bottom of the tube. The supernatant can be further centrifuged at 10,000×g for 20 minutes to pellet subcellular organelles of intermediate velocities such as mitochondria, lysosomes, and microbodies. Some of these sedimenting organelles can obtained in partial purity and are typically contaminated with other particles. Density gradient centrifugation is the preferred method to purify sub-cellular organelles and macromolecules. Placing layer can generate density gradients after layer of gradient media such as sucrose in a tube with the heaviest layer at the bottom and the lightest at the top in either a discontinuous or continuous mode. The cell fraction to be separated is placed on top of the layer and centrifuged. By using the method and/or apparatus of the invention a substantially suspended filter cake is obtained. In a further aspect of the invention the use of such substantially suspended filter cake is within the scope of the invention.

The present invention further focuses on the use of the above method and apparatus.

While centrifugation plays a vital role in biological research and manufacturing, the problem starts when very large volumes of very dilute solutions are centrifuged; since a centrifuge must run for a specific time at a very high gravity, the design of centrifuges is complex and their cost very high. Continuous flow centrifuges capable of processing of hundreds and thousands of liters of suspension cost into hundreds of thousands dollars and require very high maintenance. There is an unmet need in the art to design a method of reducing the volume of suspension substantially so that smaller size centrifuges, which cost substantially less, can be used to perform a unit operation. Fermentation tanks used for recombinant manufacturing of drugs often contain thousands of liters of media and recently processing tanks as large as 100,000 liters have been installed. The current art does not provide any solution to handle such large volumes of suspensions except, either centrifuge the entire volume or subject it to a cross-flow separation prior to centrifugation. Both of these approaches are extremely cumbersome, expensive to install and operate. The instant invention provides an ideal solution for this unmet need. Since filtration of large volumes of suspensions inevitably results in the blockage of filters and additional cost filtration apparatus that is operated under high pressure, these techniques, while useful, offer the most expensive solutions.

In the instant invention, a filtration system that comprises a hard filter surface that has pores in the size range of 5 microns or less and has a hollow surface to accumulate liquid is used. The filter is attached to a high vacuum such as a peristaltic pump or even ordinary pumps where the drawn liquid is discarded; however, any withdrawal of liquid would inevitably cause the surface of the filter to get blocked quickly and that is prevented in the instant invention by continuously scrubbing the surface of the filter with high-speed gas bubbles that continuously scarp ether surface and prevent sedimentation at the surface of the filter. By adjusting the speed of scrubbing, the filter surface can be kept clean and unblocked indefinitely allowing continuous movement of liquid but leaving the suspended particles in the container. The instant invention would therefore work whether the intent is to collect the suspended particles like bacterial and CHO cells or the filtrate containing a solution of a drug.

Similar applications are envisioned in the chemical industry, water purification industry and any such application where very fine to very crude suspended particles are to be removed from a suspension.

Figure 1A:
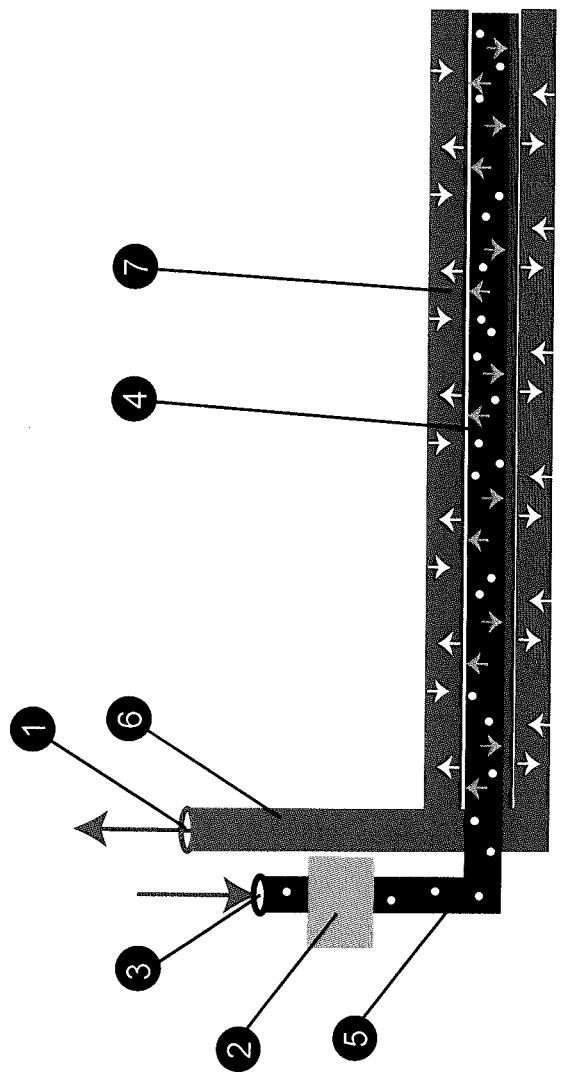

FIG. 1 shows a preferred embodiment of the concentrator filter comprising, 1: Liquid outlet; 2: filter; 3: gas inlet; 4: sparging filter; 5: gas inlet to filter; 6: concentrator filter outlet tube; 7: concentrator filter.

Figure 2:
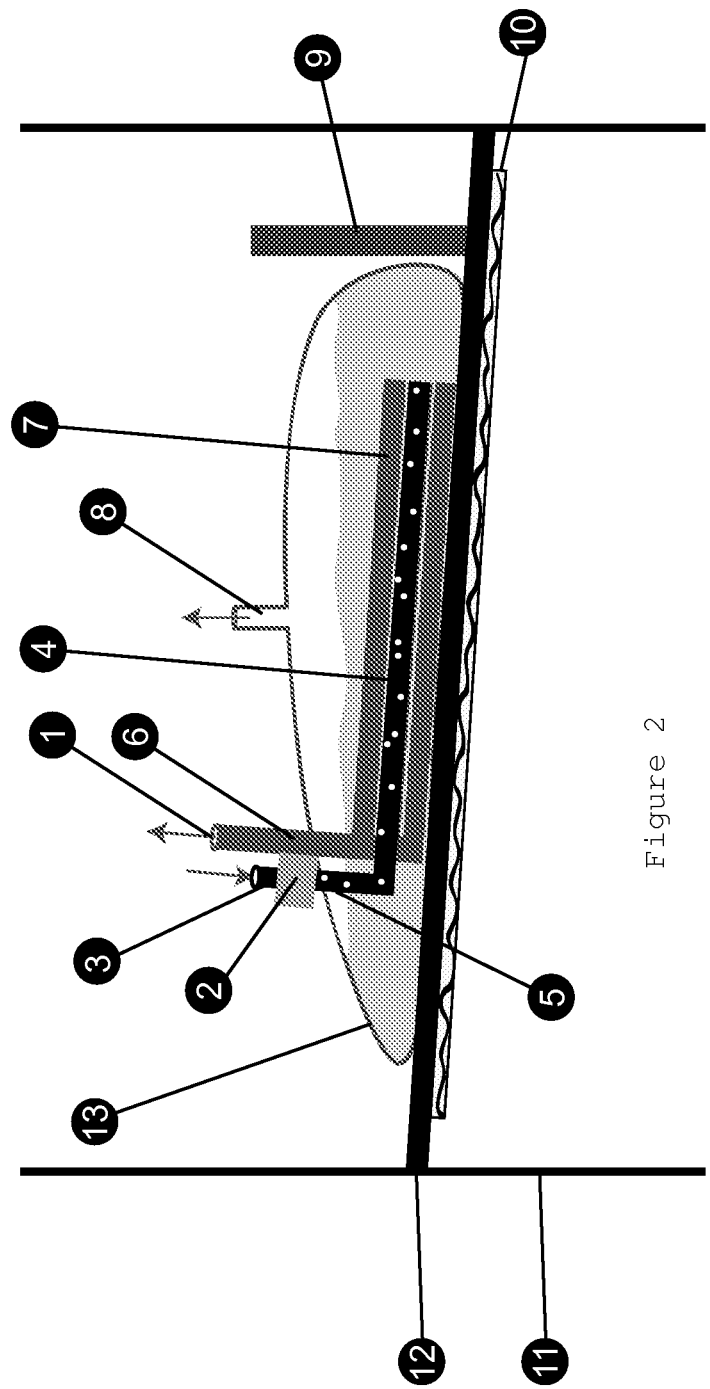
FIG. 2 is the side view of a bioreactor operating the filter assembly to concentrate the cells in the flexible bag.
Figure 3B:
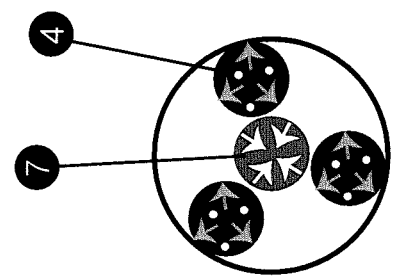
FIG. 3 (a) is the side view of a filter assembly containing concentrator filter and sparging filters surrounding the concentrator filter.
Figure 3A:
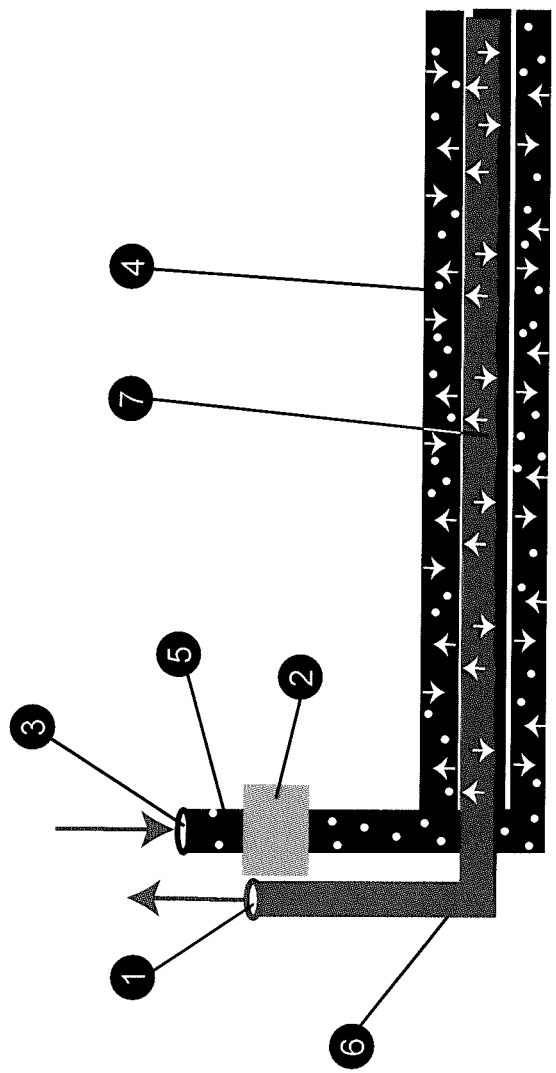

FIG. 2 shows a preferred embodiment of the use of the concentrator filter. 8: gas outlet; 9: flapper; 10: heating element; 11: vertical support; 12: lateral support; 13: flexible bioreactor.

The concentrator filter can be ideally made from a ceramic material such as aluminum oxide, the key features required are that the material be hard to withstand the pressure applied to draw the liquid without collapsing and can be formulated to provide very fine pore size such as less than 5 microns. The latter requirement is important if the intent is to remove biological entities such as bacteria and Chinese Hamster Ovary cells or to sterilize a liquid such as in water purification. The type of material used for the concentrator filter is not important as long as it can be fabricated with the above qualification.

The shape of the concentrator filter is ideally a tubular hollow element but it can be a disc, ovoid, cuboid or any shape as long as it meets the requirements of sturdiness and porosity.

It is further envisioned that the concentrator filter may be additionally covered by a nylon filter sheath to provide any desirable pore size as well as to exploit the electrical charge on the nylon sheath that might itself help to repel the suspended cells and particles from sticking to the surface if their charge is the same as the charge on the nylon membrane. As a example, Pall Corporation provides filters (www.pall.com) made of nylon that are amphoteric, positively or negatively charged at neutral pH. The Porex Company (www.porex.com) offers many interesting possibilities; for example, X-7744 T3 is a hydrophobic polyethylene sheet with a pore size of 10 Microns that can be readily wrapped around the concentrator filter.

EXAMPLES

Example 1

The device shown in FIG. 1 is inserted in a bioreactor at the end of a bioreaction cycle wherein the goal was to express erythropoietin using Chinese Hamster Ovary cells, air flow was started and the culture media withdrawn at a rate of about 5 L/minute; a total volume of 50 L was reduced to 5 liters in less than 10 minutes. Two options were exercised, first by diluting the remaining 5 L culture media with a buffer by ten times with a buffer and the buffer was continued to be drawn through the same device leaving 5 L of solution and the cells in the bioreactor containing about 1% of the active drug in the solution that was discarded. In another option, the remaining 5 L of media was subjected to a centrifuge process to remove the cells and the remaining liquid was added to the filtrate removed.

Example 2

The device shown in FIG. 1 was inserted in a bioreactor at the end of a bioreaction cycle where the aim was to grow recombinant *E. Coli* capable of expressing filgrastim, and the total volume of 50 was reduced to 5 L by removing 45 liters of the media in less than 10 minutes. This was accomplished by first turning on the air stream and then applying a vacuum by drawing the liquid using a peristaltic pump. At the end of the cycle, the 5 L media with bacterial cells was centrifuged to form a pellet mass and further processed. This obviated the need to centrifuge 50 L of media.

What is claimed is:

1. A filtration device to remove a liquid from a suspension comprising: (a) at least one concentrator filter with at least one surface and inner volume and connected to a source of vacuum through an extraction tube; (b) at least three sparging filters with at least one surface and inner volume connected to a source of compressed gas; (c) fixing the filters in a configuration to allow maximal contact of surface between filters and completely surround the concentrator filter.

2. The filtration device according to claim 1, wherein the suspension consists of a biological entity dispersed in a nutritional media.

3. The filtration device according to claim 1, wherein the filters are hollow tube, cylinder, ovoid, disc, or a cuboid.

4. The filtration device according to claim 1, wherein the filters are made of polymer, metal or ceramic material.

5. The filtration device according to claim 1, wherein the filters are made of aluminum oxide.

6. The filtration device according to claim 1, wherein a plurality of concentrator filters is assembled around a sparging filter.

* * * * *